US012628752B2

(12) United States Patent
Card et al.

(10) Patent No.: US 12,628,752 B2
(45) Date of Patent: May 19, 2026

(54) FUNGAL BIOCONTROL

(71) Applicant: Grasslanz Technology Limited, Lincoln (NZ)

(72) Inventors: Stuart Douglas Card, Palmerston North (NZ); Richard David Johnson, Palmerston North (NZ); Davood Roodi, Tehran (IR)

(73) Assignee: Grasslanz Technology Limited, Lincoln (NZ)

( * ) Notice: Subject to any disclaimer, the term of this patent is extended or adjusted under 35 U.S.C. 154(b) by 168 days.

(21) Appl. No.: 18/565,277

(22) PCT Filed: Jun. 3, 2022

(86) PCT No.: PCT/IB2022/055178
§ 371 (c)(1),
(2) Date: Nov. 29, 2023

(87) PCT Pub. No.: WO2022/254384
PCT Pub. Date: Dec. 8, 2022

(65) Prior Publication Data
US 2024/0315185 A1 Sep. 26, 2024

(30) Foreign Application Priority Data
Jun. 3, 2021 (NZ) ........................................ 776852

(51) Int. Cl.
*A01H 3/00* (2006.01)
*A01N 63/30* (2020.01)
*A01P 3/00* (2006.01)
*C12N 1/145* (2026.01)
*C12R 1/645* (2006.01)

(52) U.S. Cl.
CPC ............... *A01H 3/00* (2013.01); *A01N 63/30* (2020.01); *A01P 3/00* (2021.08); *C12N 1/145* (2021.05); *C12R 2001/645* (2021.05)

(58) Field of Classification Search
CPC ...................................................... A01H 15/00
See application file for complete search history.

(56) References Cited

PUBLICATIONS

Roodi, D. Bio-prospecting for endophytes of *Brassica* Massey University, New Zealand PhD Thesis, 180 pages (Year: 2019).*

* cited by examiner

*Primary Examiner* — David H Kruse
(74) *Attorney, Agent, or Firm* — Lewis Kohn & Walker LLP; David M. Kohn; Kari Moyer-Henry

(57) ABSTRACT

Disclosed is a strain of *Beauveria* spp. fungi which may be in a symbiotic association with a host plant, particularly a Brassicaceae host plant. Also disclosed are methods of using the disclosed *Beauveria* strain to confer resistance to at least one fungal pathogen to the host plant, as well as to combinations comprising the endophyte and a host plant or part thereof, including seeds.

8 Claims, 2 Drawing Sheets
Specification includes a Sequence Listing.

FUNGAL BIOCONTROL

RELATED APPLICATIONS

This application is a U.S. National Stage application under 35 U.S.C. § 371 from International Patent Application No. PCT/IB2022/055178 filed Jun. 3, 2022, which claims the benefit of priority from New Zealand Patent Application No. 776852 filed Jun. 3, 2021.

TECHNICAL FIELD

The present invention generally relates to a strain of *Beauveria* in a symbiotic association with a host plant, particularly a Brassicaceae host plant. The invention also relates generally to methods of using the *Beauveria* strain to confer resistance to at least one fungal pathogen to the host plant, as well as to combinations comprising the endophyte and a host plant or part thereof, including seeds.

REFERENCE TO SEQUENCE LISTING

The Sequence Listing submitted as XML file named "1064.207US_final.xml," created on Nov. 27, 2023, and having a size of 5 KB is hereby incorporated by reference pursuant to 37 C.F.R. § 1.835(a)(2).

BACKGROUND OF THE INVENTION

*Brassica* is a genus in the mustard family, Brassicaceae. Species within the genus are more commonly known as mustards or cabbages.

Crops from the genus *Brassica* were among the earliest plants to be widely cultivated by mankind (Snowdon et al., 2006).

*Brassica* displays enormous diversity and subsequently provides the widest assortment of products used by man from a single plant genus (Dixon, 2007) with many parts of the plant edible, including their buds, flowers, leaves, roots, seeds, stems and tubers (Gómez-Campo, 1980; Warwick et al., 2009).

Many species of *Brassica* are used as important animal and human food sources, as ornamentals, sources of medicines, soil conditioners, green manures, composting crops valued in bioremediation and in the production of edible and industrial oils (Dixon, 2007: Gómez-Campo, 1980; Rakow, 2004; Rao and Horn, 1995).

Domesticated species such as *Brassica oleracea* and *Brassica napus*, are now cultivated worldwide (Warwick et al., 2009), predominantly as important food crops and sources of vegetable oil, respectively.

*B. napus* seed has become one of the world's leading sources of vegetable oil and the primary oil for the production of biodiesel in Europe, with the by-product being used as a high protein animal feed (Cardone et al., 2003; Delourme et al., 2006; Körbitz, 1999).

*Brassica* species are attacked by a wide range of insect pests and pathogens that feed on the plants' stems, roots, leaves, flowers, and seeds (Dixelius et al., 2004) with little or no control options available (Granér et al., 2003).

One of the most important fungal pathogens of *Brassica* is *Leptosphaeria maculans*, which causes blackleg disease or phoma stem canker (termed "phoma" herein) (Salisbury et al., 1995; West et al., 2001). This ascomycete causes large yield losses and is a major constraint in the production of oilseed rape in Australia, Europe, New Zealand, and North America. The disease is more severe in countries with high summer temperatures.

Integrated disease management practices, including crop rotation and stubble management, are recommended to control the pathogen, with many growers also routinely relying on synthetic chemical fungicides to minimise crop losses (Salisbury et al., 1995: West et al., 2001: Zhang and Fernando, 2018). The disadvantages of the use of chemical fungicides are well known.

Additionally, although the use of resistant canola varieties was seen as promising, field populations of *L. maculans* can overcome major resistance genes within a few years, potentially accelerated by shorter crop rotations adopted by growers to capitalise on the high profits from the crop (Zhang and Fernando, 2018).

Accordingly, there is a need in the art for new methods of controlling fungal pathogens on Brassicas, particularly of controlling phoma, while avoiding some of the disadvantages associated with current control practices as described above.

It is an object of the present invention to provide at least one *Beauveria* strain fungus which when combined with a *Brassica* host plant confers the benefits of at least some level of fungal disease resistance on the host plant, and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect, the invention relates to an isolated strain of *Beauveria bassiana* that is strain O2380 (DSM Accession #33860).

In another aspect the invention relates to a composition comprising an isolated strain of *B. bassiana* strain O2380 and a carrier.

In another aspect the invention relates to a combination comprising an isolated strain of *B. bassiana* strain O2380 and a Brassicaceae host plant.

In another aspect the invention relates to a Brassicaceae host plant infected with an isolated strain of *B. bassiana* strain O2380.

In another aspect the invention relates to a method of making an artificial Brassicaceae host plant/*B. bassiana* combination comprising artificially infecting a Brassicaceae host plant with the isolated strain of *B. bassiana* strain O2380.

In another aspect the invention relates to a method of conferring at least some level of fungal disease resistance on a host plant comprising artificially infecting the host plant with an isolated strain of *B. bassiana* O2380 to form a host plant/*B. bassiana* combination.

In another aspect the invention relates to a method of controlling *Leptosphaeria maculans* on Brassicaceae host plants comprising contacting *L. maculans* with an isolated *B. bassiana* strain O2380 or with a composition comprising isolated *B. bassiana* strain O2380.

In another aspect the invention relates to isolated *B. bassiana* strain O2380 for use in controlling at least one phytopathogenic fungal strain on a Brassicaceae host plant.

In another aspect the invention relates to an isolated *B. bassiana* strain O2380 or composition comprising the isolated *B. bassiana* strain O2380 for use in controlling *Leptosphaeria maculans* on a Brassicaceae host plant.

Various embodiments of the different aspects of the invention as discussed above are also set out below in the detailed description of the invention, but the invention is not limited thereto. Other aspects of the invention may become apparent from the following description that is given by way of example only and with reference to the accompanying drawings.

BRIEF DESCRIPTION OF THE DRAWINGS

The invention will now be described by way of example only and with reference to the drawings in which:

FIGURE CAPTIONS

Figure 1:
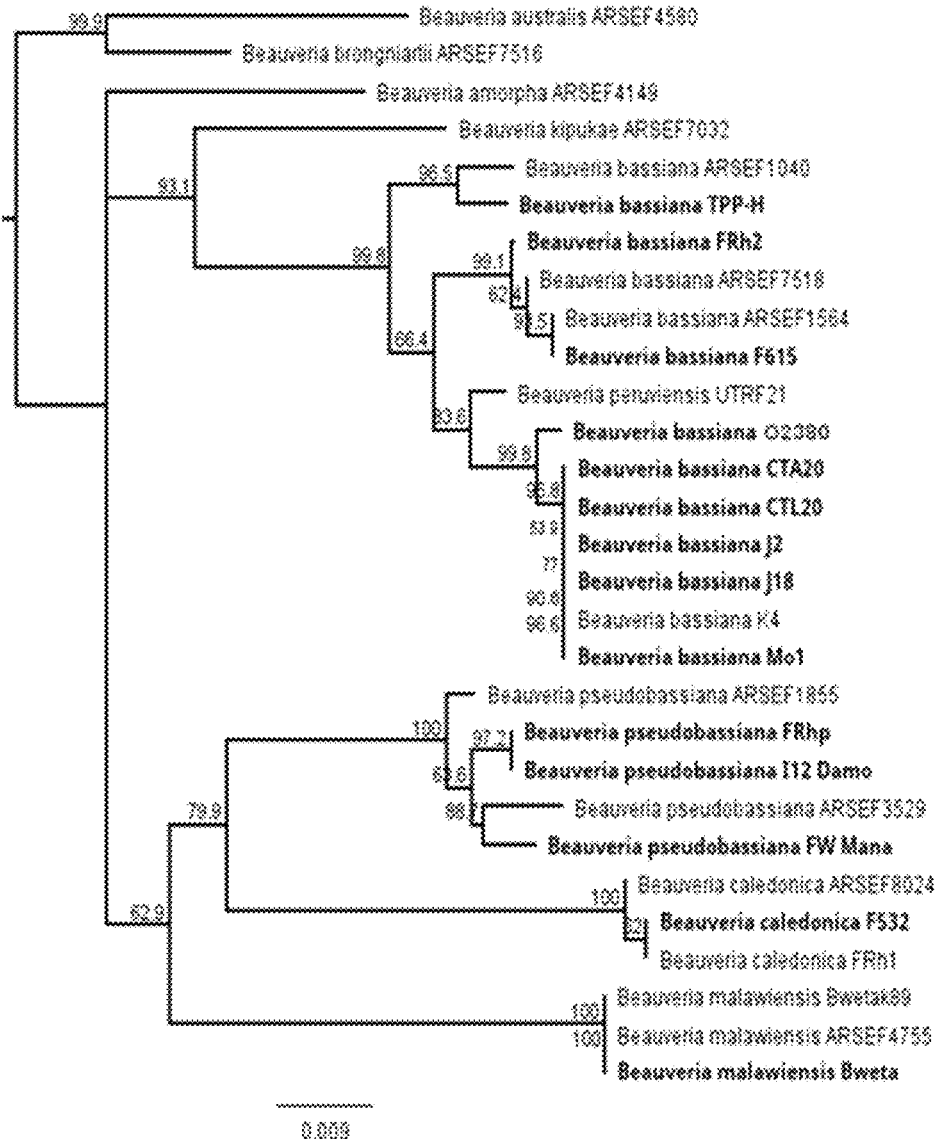

FIG. 1. Phylogenetic tree of the combined-sequence data for EF1-α and BLOC based on the Neighbor-Joining method using Juke-Cantor as a phylogenetically mathematical distance model, no outgroup, with 1000 replicates Bootstrap and the support threshold of 50% in Geneious tree builder.

Figure 2:
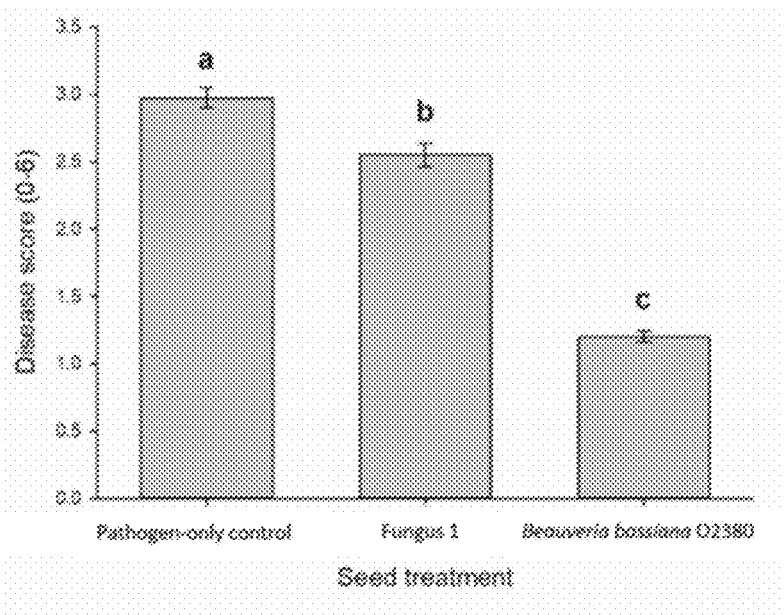
Figure 2:
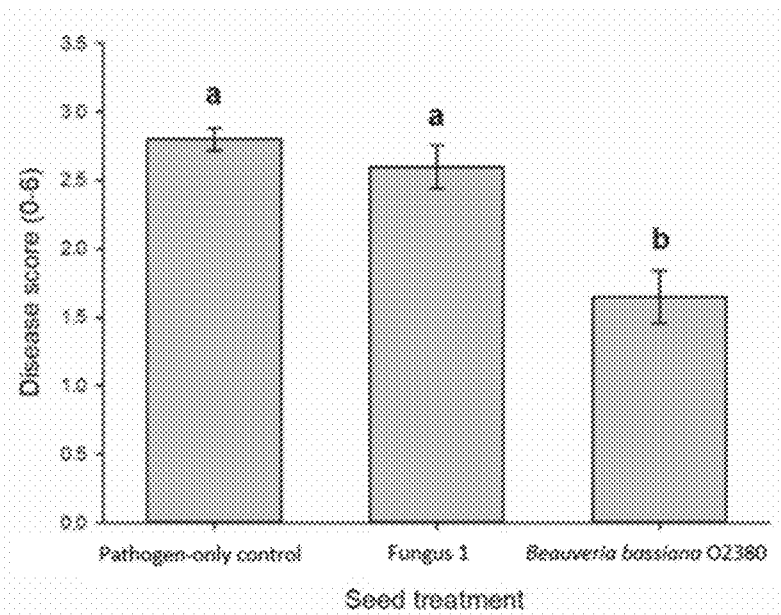

FIG. 2. Mean disease score of oilseed rape (*B. napus*), cv. Flash leaves after wounding and inoculation by *Leptosphaeria maculans* following treatment of seeds by *Beauveria bassiana* O2380 or an aqueous Tween-20® solution (pathogen-only control) (±SE). Results are presented from two replicate experiments. Bars followed by the same letter are not significantly different (P<0.05). Disease scores were assessed using a 0-6 scale whereby 0=no symptoms on wound site: 1=lesions on the wound site<1.5 mm: 2=lesions on the wound site 1.5-3.5 mm: 3=lesions on the wound site>3.0 mm: 4=grey to green tissue collapse 3.1-5.0 mm: 5=grey to green tissue collapse>5.0 mm (≤10 pycnidia): 6=grey to green tissue collapse>5.0 mm (>10 pycnidia).

DETAILED DESCRIPTION OF THE INVENTION

Definitions

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains. Examples of definitions of common terms in botany, microbiology, molecular biology and biochemistry can be found in Biology of Plants, Raven et al. (eds.), W.H. Freeman and Company, (2005): Plant Physiology, Taiz et al. (eds.), Sinauer Associates, Incorporated, (2010): Botany: An Introduction to Plant Biology, J. D. Mauseth, Jones & Bartlett Learning, (2003): Methods for General and Molecular Microbiology, 3rd Edition, C. A. Reddy et al. (eds.), ASM Press, (2008): Encyclopedia of Microbiology, 2nd ed., Joshua Lederburg, (ed.), Academic Press, (2000): Microbiology By Cliffs Notes, I. Edward Alcamo, Wiley, (1996); Dictionary of Microbiology and Molecular Biology, Singleton et al. (2d ed.) (1994): Biology of Microorganisms 11th ed., Brock et al., Pearson Prentice Hall, (2006): Biodiversity of Fungi: Inventory and Monitoring Methods, Mueller et al., Academic Press, (2004): Genes IX, Benjamin Lewin, Jones & Bartlett Publishing, (2007): The Encyclopedia of Molecular Biology, Kendrew et al. (eds.), Blackwell Science Ltd., (1994); and Molecular Biology and Biotechnology: a Comprehensive Desk Reference, Robert A. Meyers (ed.), VCH Publishers, Inc., (1995).

The term "plant or part thereof" and grammatical variations thereof as used herein encompasses whole plants and all parts of a plant from all stages of a plant life cycle including but not limited to vegetative and reproductive cells and tissues, propagules, cotyledons, seeds, embryos, shoots, in stems, leaves, leaf buds, inflorescences, flowers, flower buds, roots, anthers, ligules, palisade, mesophyll, epidermis, auricles, palea, and lemma.

The term "isolated strain" and grammatical variations thereof a used herein with reference to a fungal microorganism means that the fungal microorganism is isolated into a biologically pure culture.

The term "biologically pure culture" and grammatical variations thereof as used herein means that the culture contains a single strain of fungal microorganism. Ideally the "biologically pure culture" will not contain other organisms, including other microorganisms, although the presence of low levels of bacteria may be tolerated in some circumstances.

The term "biocontrol composition" and grammatical variations thereof as used herein refers to a composition comprising at least one biocontrol agent.

The term "biocontrol agent" and grammatical variations thereof as used herein refers to an organism that is an antagonist of one or more phytopathogenic fungi. In a preferred embodiment the biocontrol agent is a fungal biocontrol agent, preferably a phytopathogenic fungal biocontrol agent. As contemplated herein, a fungal biocontrol agent acts to confer at least some level of resistance to fungal disease on a host plant by at least reducing the duration and/or the severity of fungal disease on and/or in the host plant by a measurable amount, but not limited thereto. In some embodiments a fungal biocontrol agent confers at least some level of resistance to fungal disease to the host plant by preventing or substantially preventing fungal disease on and/or in the host plant.

The term "phytopathogenic fungus" and grammatical variations thereof as used herein means a disease-causing fungal pathogen of a *Brassica* spp. plant.

The term "fungal disease" as used herein means plant disease caused on *Brassica* spp. plants by phytopathogenic fungi. In some embodiments the phytopathogenic fungus is a *Leptosphaeria* spp. fungus, preferably *Leptosphaeria maculans*.

The terms "control" or "controlling" and grammatical variations thereof as used herein to refer to reducing, preventing, reducing, and/or eradicating fungal disease, including but not limited to inhibiting rates and extent of infections and reducing phytopathogen populations in or on plants or plant surrounds. Prevention or reduction of fungal disease may be determined by measurement of phytopathogen infection(s) or population(s) as compared to untreated phytopathogen infection(s) or population(s). Such measurements may be converted into a disease score as described herein. In some embodiments, prevention and/or reduction may be a statistically significant prevention and/or reduction in disease score as comparison to an art accepted control.

The term "effective amount" as used herein means an amount effective to protect against, delay, reduce, stabilise, improve, or treat phytopathogenic fungal infection and/or fungal disease on and/or in a plant.

The terms, "artificially infecting" and "artificial inoculation" and grammatical variations thereof as used herein encompass any infection and/or inoculation of a Brassicaceae host plant, preferably a *Brassica* spp. host plant with a strain of *B. bassiana* to form a plant/fungal symbiotic association that is not known from nature. Specifically contemplated herein the strain of *B. bassiana* that is artificially infected into and/or inoculated onto the Brassicaceae host plant is a *B. bassiana* strain that has been isolated from a wild plant of *Brassica napus* and has not been isolated from a *Brassica* cultivar.

The term "statistically significant" and grammatical variations thereof as used herein refers to the likelihood that a result or relationship is caused by something other than random chance. A result may be found to be statistically significant using statistical hypothesis testing as known and used in the art. Statistical hypothesis testing provides a "P-value" as known in the art, which represents the probability that the measured result is due to random chance alone. It is believed to be generally accepted in the art that levels of significance of 5% (0.05) or lower are considered to be statistically significant.

The term "comprising" as used in this specification means "consisting at least in part of". When interpreting statements in this specification that include that term, the features, prefaced by that term in each statement, all need to be present but other features can also be present. Related terms such as "comprise" and "comprised", and grammatical variations thereof are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DETAILED DESCRIPTION

*Beauveria bassiana* is a naturally occurring fungus associated with insects and insect habitats worldwide. *B. bassiana* is a known parasite of various arthropod species, causing white muscadine disease (Mascarin and Jaronski, 2016). *B. bassiana* has been used in various methods of biocontrol against a wide range of invertebrate pests including aphids, beetles, caterpillars, termites, *thrips*, and whitefly (Mascarin and Jaronski, 2016; Mckinnon et al., 2017; Zimmermann, 2007).

*B. bassiana* (family, Cordycipitaceae) is well known for its association with insects and insect habitats but has only recently been described as an endophyte of many dicot and monocot plant species (Lohse et al., 2015). Quite surprisingly, the inventors have determined that in addition to having bioactivity against arthropods, certain strains of *B. bassiana*, selected as isolates from wild Brassicaceae germplasm, are bioactive against fungal plant pathogens (also termed "phytopathogenic fungi" herein"). Disclosed herein is the demonstration that symbiotic associations formed between selected strains of *B. bassiana* fungi and Brassicaceae host plants, preferably *Brassica* spp. host plants, can confer on the host plant, at least some level of resistance to fungal disease.

In particular, the work disclosed herein shows that a specific strain of *B. bassiana* (strain O2380) reduces the severity of phoma stem canker (caused by the fungal plant pathogen *Leptosphaeria maculans*) on *Brassica* when used as a biocontrol agent. The observed reductions occur when *B. bassiana* O2380 is applied to the plant or part thereof at the appropriate time in the plant's life cycle.

Accordingly, in one aspect the present invention relates to an isolated strain of *B. bassiana* strain O2380 (DSM Accession #33860).

The *B. bassiana* endophyte strain described herein was isolated from a wild *Brassica napus* plant collected in California and was deposited at the Leibniz Institute, DSMZ-German Collection of Microorganisms and Cell Cultures GmbH, Inhoffenstraße 7B, 38124 Braunschweig, Germany on the following dates for strains:

> *B. bassiana* O2380 (DSM #33860) on the 26 Apr. 2021, according to the Budapest Treaty for purposes of patent procedure.
>
> *B. bassiana* strain O2380 as described herein was isolated from endophyte-infected *Brassica* plants. Seed were first surface disinfected for five min in 5% aqueous Tween-20® solution (Sigma-Aldrich Inc., Auckland, New Zealand), two min in 70% ethanol, 10 min in 0.5% sodium hypochlorite, one min in 70% ethanol and rinsed three times in sterile water. Seed were then dried on filter paper (110 mm, Thermo Fisher Scientific Ltd., Auckland, New Zealand) within a sterile environment and stored at 4° C. in the dark. To induce germination, seeds were dipped into sterile 0.2% KNO3 solution and immediately plated onto Petri plates containing 1.5% water agar (WA), with 10 seeds per plate. Petri plates were incubated at 4° C. in the dark for 72 h to break seed dormancy. Dormant accessions (as tested for 15 accessions) resulted in either zero or poor germination without this process and were subsequently transferred to a custom-built growth chamber at 22-25° C. and a 16/8 h (light/dark) photoperiod.

Seed and the subsequent seedlings were examined daily under a dissecting microscope and those exhibiting any obvious epiphytic microbial growth were discarded. After 2-3 days, 10 clean seedlings, from each accession, were transferred to sterile tissue culture pots, 98 mm diameter (2105646, Alto Ltd., New Zealand) containing Murashige & Skoog (MS) basal salts (Murashige & Skoog, 1962) with minimal organics (Sigma-Aldrich, New Zealand), plus 3% sucrose and 1.5% agar (Ali et al., 2007).

Pots were placed in the growth chamber at 22-25° C. and a 16/8 h (light/dark) photoperiod and visually assessed every day for a month using a dissecting microscope. Plants were discarded if they showed any disease symptoms or any saprophytic microbial growth. Four clean seedlings were finally selected from each accession and subsequently dissected into two components: shoot and root. These organs were further dissected into 2-3 mm² pieces using sterile forceps and a scalpel. Ten pieces per organ type from each seedling were transferred to Petri plates containing NA. Petri plates were incubated for 3 weeks at 22° C. in the dark and checked daily under a dissecting microscope for microbial growth. Fungal colonies fitting the descriptions of *Beauveria* were selected and sub-cultured on PDA before storing in 25% glycerol at −80° C. within an ultra-low temperature (ULT) freezer.

Once isolated, the isolated and/or biologically pure fungus may be cultured using standard techniques as known in the art and as disclosed herein, including in the examples.

In one embodiment, *B. bassiana* is cultured on potato dextrose agar (PDA) between 20° C. and 25° C., preferably between 21° C. and 23° C. The optimal temperature for growth of the fungus is 22° C. Growth of the fungus at temperatures above or below this range may be possible although growth may be reduced or may cease entirely. In one embodiment, the fungus is cultured in the dark.

Strain O2380 exhibits slow growing white colonies on PDA at 22° C. After 3-4 days incubation the culture produces single-celled, near-spherical, hyaline conidia (spores) formed on a zig-zag conidiophore, or rachis, characteristic of *Beauveria* spp.

In one embodiment the isolated *B. bassiana* strain O2380 is in biologically pure culture.

In one embodiment the biologically pure culture is completely free of any other microorganisms.

In one embodiment the biologically pure culture is completely free other fungi and is substantially free of any other microorganisms.

In another aspect the invention relates to a composition comprising an isolated strain of *B. bassiana* strain O2380 and a carrier.

Compositions may be prepared using standard techniques known in the art and as described in the examples herein. In one embodiment the hyphae or parts thereof in the composition are prepared by macerating the hyphae and/or mycelia of *B. bassiana* strain O2380 and collecting the spores as described herein.

In one embodiment the composition is a biocontrol composition.

In one embodiment the biocontrol composition comprises an effective amount of *B. bassiana* strain O2380 to control at least one phytopathogenic fungus on and/or in a host plant.

In one embodiment the at least one phytopathogenic fungus is a *Leptosphaeria* spp. fungus, preferably *Leptosphaeria maculans*.

In one embodiment the biocontrol composition comprises an effective amount of *B. bassiana* strain O2380 to confer at least some level of resistance to fungal disease to a host plant.

In one embodiment the fungal disease is a fungal disease caused by a *Leptosphaeria* spp. fungus, preferably by *Leptosphaeria maculans*.

In one embodiment the composition comprises spores of *B. bassiana* strain O2380. In one embodiment the composition consists essentially of spores of *B. bassiana* strain O2380.

In one embodiment the composition comprises at least $1\times10$, $1\times10^2$, $1\times10^3$, $1\times10^4$, $1\times10^5$, $1\times10^6$, $1\times10^7$, or $1\times10^8$ spores/mL. In one embodiment the composition comprises at least $1\times10^5$ or at least $1\times10^6$ spores/mL, preferably at least $1\times10^6$ spores/mL.

In one embodiment the composition consists essentially of at least $1\times10$, $1\times10^2$, $1\times10^3$, $1\times10^4$, $1\times10^5$, $1\times10^6$, $1\times10^7$, or $1\times10^8$ spores/mL. In one embodiment the composition consists essentially of at least $1\times10^5$ or at least $1\times10^6$ spores/mL, preferably at least $1\times10^6$ spores/mL.

In one embodiment the composition comprises about $1\times10$, $1\times10^2$, $1\times10^3$, $1\times10^4$, $1\times10^5$, $1\times10^6$, $1\times10^7$, or $1\times10^8$

8 spores/mL. In one embodiment the composition comprises about $1\times10^5$ or about $1\times10^6$ spores/mL, preferably about $1\times10^6$ spores/mL.

In one embodiment the composition consists essentially of about $1\times10$, $1\times10^2$, $1\times10^3$, $1\times10^4$, $1\times10^5$, $1\times10^6$, $1\times10^7$, or $1\times10^8$ spores/mL. In one embodiment the composition consists essentially of about $1\times10^5$ or about $1\times10^6$ spores/mL, preferably about $1\times10^6$ spores/mL.

In one embodiment the composition comprises about $1\times10$ to about $1\times10^9$ spores/mL, about $1\times10^2$ to about $1\times10^8$, about $1\times10^3$ to about $1\times10^7$, preferably about $1\times10^4$ to about $1\times10^6$ spores/mL.

In one embodiment the composition consists essentially of about $1\times10$ to about $1\times10^9$ spores/mL, about $1\times10^2$ to about $1\times10^8$, about $1\times10^3$ to about $1\times10^7$, preferably about $1\times10^4$ to about $1\times10^6$ spores/mL.

In one embodiment the carrier is an agriculturally acceptable carrier.

In one embodiment the agriculturally acceptable carrier is selected from the group consisting of antioxidants, wetting agents, emulsifiers, fillers, growth stimulants, anti-caking agents, dispersants, surfactants and combinations thereof. In one embodiment the agriculturally acceptable carrier is water.

In one embodiment the composition comprises an agriculturally acceptable adjuvant. In one embodiment the agriculturally acceptable adjuvant is selected from the group consisting of an additional active agent and a formulation agent.

In one embodiment the agriculturally acceptable adjuvant is one or more additional active agents. In one embodiment the agriculturally acceptable adjuvant is one or more formulation agents.

In one embodiment the composition comprises a combination of one or more additional active agents and one or more formulation agents. In some embodiments the composition is formulated as pre-prepared composition or in a concentrated form. In some embodiments the composition comprises a solid or a liquid formulation.

Any suitable formulation agent(s) may be used as known in the art. For example, a suitable formulation agent may be a compound or other material that facilitates or optimizes the production, handling, storage, transport, application and/or persistence of the composition or of the constituents of the composition, or for use in the invention on plants or on parts thereof, but not limited thereto.

Particularly suitable formulation agents include surfactants, dispersants, preservatives, wetting agents, emulsifiers, humectants, stickers, spreaders, stabilizers, penetrants, adhesion agents, pH buffers, and nutrients, either alone or in various combinations as may be determined by the skilled worker.

In another aspect the invention relates to a combination comprising an isolated strain of *B. bassiana* strain O2380 and a Brassicaceae host plant.

In one embodiment the Brassicaceae host plant is a *Brassica* spp. host plant.

In one embodiment the *Brassica* spp. host plant is selected from the group consisting of *Brassica balearica* (Mallorca cabbage); *Brassica carinata* (Abyssinian mustard or Abyssinian cabbage); *Brassica elongate* (elongated mustard); *Brassica fruticulose* (Mediterranean cabbage); *Brassica hilarionis* (St. Hilarion cabbage); *Brassica juncea* (Indian mustard, brown and leaf mustards, Sarepta mustard); *Brassica napus* (rapeseed, canola, rutabaga, Siberian kale); *Brassica narinosa* (broadbeaked mustard); *Brassica nigra* (black mustard); *Brassica oleracea* (kale, cabbage, collard greens, broccoli, cauliflower, kai-lan, Brussels sprouts, kohlrabi); *Brassica perviridis* (tender green, mustard spinach); *Brassica rapa* syn. *B. campestris* (Chinese cabbage, turnip, rapini, komatsuna); *Brassica rupestris* (brown mustard); *Brassica spinescens* and *Brassica tournefortii* (Asian mustard).

In one embodiment the *Brassica* spp. is *B. napus, B. rapa. B. campestris* or *B. oleracea.*

In one embodiment the *Brassica* spp. is a forage *Brassica.*

In one embodiment the *Brassica* spp. host plant is a subspecies or interspecific hybrid between any combination of *B. napus, B. rapa. B. campestris* and/or *B. oleracea.*

In one embodiment the *Brassica* spp. is selected form the group consisting of *B. campestris* ssp. *rapifera, B. napus* ssp. *biennis×B. oleracea* ssp. *acephala, B. oleracea* ssp. *acephala, B. napus* subsp. *napus*, and *B. napus* ssp. *biennis.*

In one embodiment the *B. campestris* ssp. *rapifera* is cv. Hunter.

In one embodiment the *B. napus* ssp. *biennis×B. oleracea* ssp. *acephala* is cv. Titan. In one embodiment the *B. oleracea* ssp. *acephala* is cv. Regal or cv. Firefly.

In one embodiment the *B. napus* subsp. *napus* is cv. King.

In another aspect the invention relates to a Brassicaceae host plant infected with an isolated strain of *B. bassiana* strain O2380.

In one embodiment the Brassicaceae host plant is infected with an effective amount of *B. bassiana* strain O2380.

Specifically contemplated as embodiments of this aspect of the invention that is a combination comprising an isolated strain of *B. bassiana* strain O2380 and a Brassicaceae host plant, are all of the embodiments related to the isolated *B. bassiana* strain O2380, the compositions comprising the isolated *B. bassiana* strain O2380 and the Brassicaceae host plants as set forth in the previous aspects of the invention.

In another aspect the invention relates to a method of making an artificial Brassicaceae host plant/*B. bassiana* combination comprising artificially infecting a Brassicaceae host plant with the isolated strain of *B. bassiana* strain O2380.

In one embodiment artificially infecting comprises contacting the host plant with the isolated *B. bassiana* strain O2380 or with a composition comprising the isolated *B. bassiana* strain O2380.

In one embodiment contacting comprises spraying, drenching or coating the host plant or part thereof. In one embodiment the host plant is a mature host plant.

In one embodiment the part thereof is a stem, shoot, leaf, or seed, preferably a seed.

In one embodiment contacting comprises coating or soaking the seed of the host plant. In one embodiment contacting comprises coating the seed of the host plant. In one embodiment contacting comprises soaking the seed of the host plant.

Seeds of the selected *Brassica* cultivar were surface disinfected by washing for five min in 5% aqueous Tween® 20 solution (Sigma-Aldrich Inc., New Zealand), two min in 70% ethanol, 10 min in 2% sodium hypochlorite, one min in 70% ethanol and rinsed three times in sterile tap water. Seeds were then dried on filter paper (110 mm, ThermoFisher Scientific Inc., LabServ®, USA) within a sterile environment and stored at 4° C. until use.

In one embodiment contacting is from about 10 seconds to about 1 week.

In one embodiment contacting is for about 10 seconds, about 30 seconds, about 1 minute, about 5 min, about 10 min, about 15 min, about 20 min, about 30 min, about 1 h, about 2 h, about 3 h, about 4 h, about 5 h, about 6 h, about 12 h, about 24 h, about 36 h, about 48 h, about 72 h, about 1 week.

Specifically contemplated as embodiments of this aspect of the invention that is a method of making an artificial Brassicaceae host plant/*B. bassiana* combination, are all of the embodiments related to the isolated *B. bassiana* strain O2380, the compositions comprising the isolated *B. bassiana* strain O2380 and the Brassicaceae host plants, the combinations comprising an isolated strain of *B. bassiana* strain O2380 and a Brassicaceae host plant as set forth in the previous aspects of the invention.

In another aspect the invention relates to a method of conferring at least some level of fungal disease resistance on a Brassicaceae host plant comprising artificially infecting the host plant with an isolated strain of *B. bassiana* strain O2380 to form a host plant/*B. bassiana* combination.

In one embodiment artificially infecting the host plant comprises contacting the host plant with the isolated *B. bassiana* strain O2380 or a composition comprising this strain. Specifically contemplated here are all of the contacting embodiments set out in the previous aspect of the invention related making an artificial Brassicaceae host plant/*B. bassiana* combination.

In one embodiment the level of fungal disease resistance conferred is a reduction in the disease score of a plant or part thereof that has been treated with the isolated *B. bassiana* strain O2380 or composition described herein when compared to an untreated control plant or part thereof. In one embodiment the disease score is an integer between 0 and 6, and the reduction is a reduction of at least 1, preferably of at least 1.1, at least 1.15, at least 1.8, preferably at least 1.9.

The term "disease score" as used herein means a measurement assigned to a plant when assessing the extent of *L. maculans* infection on that plant using the following scale: 0-6 scale whereby 0=no symptoms on wound site: 1=lesions on the wound site<1.5 mm: 2=lesions on the wound site 1.5-3.5 mm: 3=lesions on the wound site>3.0 mm: 4=grey to green tissue collapse 3.1-5.0 mm: 5=grey to green tissue collapse>5.0 mm (≤10 pycnidia): 6=grey to green tissue collapse>5.0 mm (>10 pycnidia).

For example, the experiments conducted with *B. bassiana* strain O2380 as disclosed herein showed a drop in the disease score of treated plants or parts thereof as compared to untreated control plants or parts thereof of from 4.2 to 3.1, from 3.6 to 1.7, from 3 to 1.2, and from 2.8 to 1.65.

In one embodiment the Brassicaceae host plant is a *Brassica* spp. as contemplated herein for other aspects of the invention, particularly *B. napus, B. rapa, B. campestris* and/or *B. oleracea* and/or a subspecies or interspecific hybrid between any combination of these *Brassica* spp.

In one embodiment the fungal pathogen on the Brassicaceae host plant causes phoma stem canker. In one embodiment the fungal pathogen is *Leptosphaeria maculans.*

Specifically contemplated as embodiments of this aspect of the invention that is a method of conferring at least some level of fungal disease resistance on a Brassicaceae host plant, are all of the embodiments related to the isolated *B. bassiana* strain O2380, the compositions and combinations comprising the isolated *B. bassiana* strain O2380 and the Brassicaceae host plants, and the methods of making an artificial Brassicaceae host plant/*B. bassiana* combination as set forth in the previous aspects of the invention.

In another aspect the invention relates to a method of controlling *Leptosphaeria maculans* on Brassicaceae spp. host plants comprising contacting *L. maculans* with an isolated *B. bassiana* strain O2380 or with a composition comprising isolated *B. bassiana* strain O2380. In one embodiment the composition consists essentially of the isolated *B. bassiana* strain O2380.

Specifically contemplated as embodiments of this aspect of the invention that is a method of controlling *Leptosphaeria maculans* on Brassicaceae spp. host plants, are all of the embodiments related to the isolated *B. bassiana* strain O2380, the compositions and combinations comprising the isolated *B. bassiana* strain O2380 and the Brassicaceae host plants, the methods of making an artificial Brassicaceae host plant/*B. bassiana* combination, and methods of conferring at least some level of fungal disease resistance on a Brassicaceae host plant as set forth in the previous aspects of the invention.

In another aspect the invention relates to isolated *B. bassiana* strain O2380 for use in controlling at least one phytopathogenic fungal strain on a Brassicaceae host plant. In one embodiment the phytopathogenic fungal strain is *L. maculans*. In one embodiment controlling comprises contacting as described herein for any other aspect of the invention. Also specifically contemplated as embodiments of this aspect of the invention are all of the embodiments related to the isolated *B. bassiana* strain O2380, the compositions and combinations comprising the isolated *B. bassiana* strain O2380 and the Brassicaceae host plants, the methods of making an artificial Brassicaceae host plant/*B. bassiana* combination, and methods of conferring at least some level of fungal disease resistance on a Brassicaceae host plant as set forth in the previous aspects of the invention.

In another aspect the invention relates to an isolated strain of *B. bassiana* strain O2380 or composition comprising the isolated *B. bassiana* strain O2380 for use in controlling *Leptosphaeria maculans* on a Brassicaceae host plant. In one embodiment controlling comprises contacting as described herein for any other aspect of the invention. Also specifically contemplated as embodiments of this aspect of the invention are all of the embodiments related to the isolated *B. bassiana* strain O2380, the compositions and combinations comprising the isolated *B. bassiana* strain O2380 and the Brassicaceae host plants, the methods of making an artificial Brassicaceae host plant/*B. bassiana* combination, and methods of conferring at least some level of fungal disease resistance on a Brassicaceae host plant as set forth in the previous aspects of the invention.

Various aspects of the invention will now be illustrated in non-limiting ways by reference to the following examples.

EXAMPLES

Example 1

Isolation of *B. bassiana*
Source and Geographic Origin of *B. bassiana* Strain O2380.

*B. bassiana* strain O2380 as described herein was obtained from a *Brassica rapa* host plant accession (Ames 30081) held by the United States Department of Agriculture, Agricultural Research Services, Iowa State University Regional Plant Introduction Station. The plant germplasm was collected from the wild in California in 2009 and received by the U.S. National Plant Germplasm System (NPGS) on the 15 Sep. 2009 as seed.

Example 2

Detection of Genetic Variation of *Beauveria* Strains

Sequences of 28 *Beauveria* isolates were compared to that of strain O2380 using both elongation factor 1 alpha (EF1-α) and B locus intergenic region (Bloc) markers (Table 1). For PCR, *Beauveria* strain O2380 was incubated at 22° C. for two weeks before fungal DNA was extracted using Quick-DNA™ Fungal/Bacterial Kit (Zymo Research Corporation, USA) and quantified using the Invitrogen Qubit™ 4 Fluorometer (ThermoFisher Scientific Inc., USA). The 25 μL PCR reaction mixture consisted of: 15.75 μL sterile water, 2.5 μL buffer (10×) plus MgCl2 (2 mM), 2 μL deoxynucleotide (dNTP's) (2.5 mM), 0.25 μL Fast start polymerase Taq, 1 μL of each primer, 0.5 μL bovine serum albumin (Bio Labs® Inc., New Zealand) and 2 μL of extracted DNA per sample. Thermocycling conditions were set as 95° C. for 5 min followed by 40 cycles of (95° C. for 45 s, 57° C. for 45 s, 72° C. for 2 min) and a final extension of 72° C. for 7 min.

Sequence data from O2380, and the other *Beauveria* strains used in this study, were imported into the computer software Geneious Prime® 2021.0.1 (Biomatters Ltd., New Zealand) (Kearse et al., 2012). The forward and reverse directions from the same sequence were assembled using de novo assembly to combine contigs into larger consensus reads (Bridgeman et al., 2020). The consensus result of each isolate was identified using the Nucleotide Basic Local Alignment Search Tool for standard nucleotides (BLASTn) (Altschul et al., 1990). All consensus data from EF1-α and Bloc were then aligned using the Clustal Omega computer program (Sievers & Higgins, 2018). After aligning, longer sequences were manually trimmed to adjust the length of the shortest sequence. Trimmed results were concatenated manually for phylogenetic analysis. The consensus tree (FIG. 1) was built from the combined sequence alignment by Neighbor-Joining as nucleotide substitution (Saitou & Nei, 1987) using Jukes-Cantor (Jukes & Cantor, 1969) as phylogenetically mathematics distance model, no outgroup, with 1000 replications Bootstrap and a support threshold of 50% in Geneious tree builder (Biomatters Ltd., New Zealand).

Several strains of *B. bassiana* (sensu stricto) were similar to that from accession O2380 (FIG. 1), confirming its species identity and its genetic distinctness from other *B. bassiana* strains.

TABLE 1

| | | Primer sequences | | | |
|---|---|---|---|---|---|
| Marker | Primer name | Sequence (5'-3') | SEQ ID NO: | | |
| EF1-α | 983F | CARGAYGTBTACAAGATYGGTGG | 1 | Cummings, |
| | 2218R | CCRAACRGCRACRGTYYGTCTCAT | 2 | 2009; Glare et al., 2008; Rehner & Buckley, 2005 |

TABLE 1-continued

| | | Primer sequences | | |
|---|---|---|---|---|
| Marker | Primer name | Sequence (5'-3') | SEQ ID NO: | |
| Bloc | B22U | GTC GCA GCC AGA GCA ACT | 3 | Fisher et al., |
| | B822L | AGA TTC GCA ACG TCA ACT T | 4 | 2011; Korosi et al., 2019; Rehner et al., 2006 |

Example 3

Isolation of Fungal Endophyte Strains

*B. bassiana* O2380 was isolated from an accession of *Brassica rapa* as described in Example 1.

Seed were first surface disinfected for five min in 5% aqueous Tween-20® solution (Sigma-Aldrich Inc., Auckland, New Zealand), two min in 70% ethanol, 10 min in 0.5% sodium hypochlorite, one min in 70% ethanol and rinsed three times in sterile water. Seed were then dried on filter paper (110 mm, Thermo Fisher Scientific Ltd., Auckland, New Zealand) within a sterile environment and stored at 4° C. in the dark. To induce germination, seeds were dipped into sterile 0.2% KNO3 solution and immediately plated onto Petri plates containing 1.5% water agar (WA), with 10 seeds per plate. Petri plates were incubated at 4° C. in the dark for 72 h to break seed dormancy. Dormant accessions (as tested for 15 accessions) resulted in either zero or poor germination without this process and were subsequently transferred to a custom-built growth chamber at 22-25° C. and a 16/8 h (light/dark) photoperiod.

Seed and the subsequent seedlings were examined daily under a dissecting microscope and those exhibiting any obvious epiphytic microbial growth were discarded. After 2-3 days, 10 clean seedlings, from each accession, were transferred to sterile tissue culture pots, 98 mm diameter (2105646, Alto Ltd., New Zealand) containing Murashige & Skoog (MS) basal salts (Murashige & Skoog, 1962) with minimal organics (Sigma-Aldrich, New Zealand), plus 3% sucrose and 1.5% agar (Ali et al., 2007).

Pots were placed in the growth chamber at 22-25° C. and a 16/8 h (light/dark) photoperiod and visually assessed every day for a month using a dissecting microscope. Plants were discarded if they showed any disease symptoms or any saprophytic microbial growth. Four clean seedlings were finally selected from each accession and subsequently dissected into two components: shoot and root. These organs were further dissected into 2-3 mm² pieces using sterile forceps and a scalpel. Ten pieces per organ type from each seedling were transferred to Petri plates containing NA. Petri plates were incubated for 3 weeks at 22° C. in the dark and checked daily under a dissecting microscope for microbial growth. Fungal colonies fitting the descriptions of *Beauveria* were selected and sub-cultured on PDA before storing in 25% glycerol at −80° C.

Example 4

Fungal Description

Strain O2380 exhibits slow growing white colonies on PDA at 22° C. After 3-4 days incubation the culture produces single-celled, near-spherical, hyaline conidia (spores) formed on a zig-zag conidiophore, or rachis, characteristic of *Beauveria* spp.

Example 5

Inoculation of *B. bassiana* onto *Brassica* Seed

Seeds of the selected *Brassica* cultivar were surface disinfected by washing for five min in 5% aqueous Tween® 20 solution (Sigma-Aldrich Inc., New Zealand), two min in 70% ethanol, 10 min in 2% sodium hypochlorite, one min in 70% ethanol and rinsed three times in sterile tap water. Seeds were then dried on filter paper (110 mm, ThermoFisher Scientific Inc., LabServ®, USA) within a sterile environment and stored at 4° C. until use.

*Beauveria* strain O2380 was removed from the ultra-low temperature (ULT) freezer and defrosted at room temperature before plating onto PDA (CM0139, Oxoid Limited, UK). Petri plates containing the fungus were then incubated for approximately two weeks at 22° C. in the dark to promote mycelial growth and sporulation. Subsequent spores (conidia) of the *Beauveria* were dislodged by adding 50 mL of sterile water to the Petri plate and gently brushing the fungal colony with a sterile loop. The resulting crude suspension was passed through a single layer of sterile Miracloth (Sigma-Aldrich Inc., New Zealand) to remove mycelial fragments and one drop of Tween-20® was added to the solution to stop the spores adhering together. The concentration of the spore suspension was estimated using a haemocytometer and adjusted to $10^6$ spores per mL. The viability of fungal spores was assessed by spraying diluted aliquots of the prepared spore suspensions on fresh PDA and counting the subsequent colonies after 3 days of incubation at 22° C. in the dark.

Disinfected seeds of the selected *Brassica* cultivar were soaked in the *Beauveria* spore suspension for 10 min at room temperature. All treated seed then were transferred to sterile filter papers and allowed to dry at room temperature for 30 min. Seed were sown in a vermiculite growth medium supplemented with essential nutrients to support plant growth, including necessary macro and micronutrients, in the form of a nutrient solution following the manufacturer's instructions (Thrive, Yates New Zealand). In each pot, measuring 10×15 cm, 10 seeds were sown, which were later thinned to three seedlings per pot after germination. Pots were subsequently placed in a glasshouse with natural light at 20-25° C. and watered as required. Plant health, development, and any visible disease symptoms were assessed daily.

Example 6

The Effect of *B. bassiana* Strain O2380 on Phoma Stem Canker

The bioactivity of *Beauveria* strain O2380 was assessed in planta against the plant pathogen, *Leptosphaeria maculans*. *Leptosphaeria maculans* strain LUPP2376 is a highly pathogenic strain originally identified and isolated from a diseased swede (*Brassica napobrassica*) collected in Gore, New Zealand (Lob, 2014). After sub-culturing on PDA, strain LUPP2376 was stored in 30% glycerol at −80° C. until use. Previous work noted that strain LUPP2376 was highly pathogenic towards oilseed rape (*B. napus*), cv. Flash (Lob, 2014) and therefore initial bioactivity trials utilised this susceptible cultivar of *Brassica*. Strain LUPP2376 was defrosted at room temperature and plated onto PDA. Petri plates containing the pathogen were subsequently incubated for two weeks at 15-20° C. with a 16/8 hr (light/dark) photoperiod. A spore suspension of the pathogen was then prepared as described for *B. bassiana* at a concentration of $10^7$ spores per ml. The viability of *L. maculans* spores were assessed by spraying aliquots of the prepared spore suspension on fresh PDA and observing the developing colonies after 5 days incubation at 18° C. in the dark.

Seed of oilseed rape were surface disinfected and inoculated with the two fungal endophytes as described earlier. Control seed were only treated with a sterile aqueous Tween-20® solution. Seed from all treatment groups were then placed on sterile filter paper to dry and later transferred to sterile plastic plant containers (product number 2105646, Alto Limited, New Zealand) containing autoclaved vermiculite. Subsequently, seedlings were planted in seedling trays containing autoclaved potting mix within Saxon mini greenhouses (Bunnings Group, Australia). The mini greenhouses were closed with a lid, sealed with plastic tape to keep humidity in the tray elevated and placed in a controlled environment (A1000, Conviron Asia Pacific Pty Limited, Australia) at 18° C. with a 16/8 hr (light/dark) photoperiod. At the cotyledon leaf stage, one cotyledon leaf per seedling was punctured with a sterile needle and 15 µL of the *L. maculans* spore suspension was placed on the wound site using a pipette. Plants were incubated, as described earlier, for two weeks to allow disease symptoms to appear and subsequently assessed using a 0-6 scale as described by Hammoudi et al., (2012): 0=no symptoms: 1=lesions on the infection site<1.5 mm: 2=lesions on the infection site 1.5-3.5 mm: 3=lesions on the infection site>3.0 mm: 4=grey to green tissue collapse 3.1-5.0 mm: 5=grey to green tissue collapse>5.0 mm (≤10 pycnidia): 6=grey to green tissue collapse>5.0 mm (>10 pycnidia). The mean score from 10 infected seedlings from each tray was used in the analysis.

Statistical analyses were performed using the software package R (R Core Team, 2019). A cumulative link mixed model (CLMM) from the "ordinal" R package was used to model the lesion severity scores using an equidistant threshold. The fixed effects used in the model were the treatment group, time (as a factor), and their interaction term. Random intercepts were used for each plant replicate. Analysis of Deviance was used to assess the significance of the fixed effects and their interaction terms. Newly emerging leaves were carefully removed during the experimental period and the experiment was repeated once. There were three treatments (seed treated with two fungal endophytes, and an aqueous Tween-20® solution acting as a pathogen only control), with 10 seedlings per treatment arranged in a randomised design.

*B. bassiana* O2380 significantly (P<0.05) suppressed the amount of disease caused by *L. maculans* on leaves of oilseed rape (*B. napus*), cv. Flash after wounding, across two replicated experiments, compared to the pathogen-only control (FIG. 2).

Disclosed herein is the inventors surprising determination that *B. bassiana* strain O2380 is an effective biocontrol agent against *Leptosphaeria maculans*, the fungal pathogen responsible for the disease phoma stem canker (or blackleg disease) in *Brassica* spp.

Example 7

The bioactivity of *B. bassiana* strain O2380 on phoma stem canker compared to other strains of *B. bassiana* and *B. pseudobassiana*

The bioactivity of *Beauveria* strain O2380 was assessed in planta against the plant pathogen, *Leptosphaeria maculans. Leptosphaeria maculans* strain LUPP2376 is a highly pathogenic strain originally identified and isolated from a diseased swede (*Brassica napobrassica*) collected in Gore, New Zealand (Lob, 2014). After sub-culturing on PDA, strain LUPP2376 was stored in 30% glycerol at −80° C. until use. Previous work noted that strain LUPP2376 was highly pathogenic towards oilseed rape (*B. napus*), cv. Flash (Lob, 2014). Strain LUPP2376 was defrosted at room temperature and plated onto PDA. Petri plates containing the pathogen were subsequently incubated for two weeks at 15-20° C. with a 16/8 hr (light/dark) photoperiod. A mycelial suspension of the pathogen was then prepared a concentration of approximately $10^8$ CFU per ml. The viability of *Leptosphaeria maculans* spores were assessed by spraying aliquots of the prepared spore suspension on fresh PDA and observing the developing colonies after 5 days incubation at 18° C. in the dark.

Seed of forage kale, cv. Firefly, were surface disinfected and coated with the fungal treatments. Control seed were only treated with the coating formula and contained no viable fungus. Seed from all treatment groups were placed in separate Petri dishes containing autoclaved vermiculite (one Petri plate per treatment). Subsequent seedlings were planted in seedling trays containing autoclaved potting mix within Saxon mini greenhouses (Bunnings Group, Australia). The mini greenhouses were closed with a lid, to keep humidity in the tray elevated and placed in a controlled temperature room at 18° C. with a 16/8 hr (light/dark) photoperiod. At the cotyledon leaf stage, one cotyledon leaf per seedling was punctured with a sterile needle and 15 µL of the *Leptosphaeria maculans* suspension was placed on the wound site using a pipette. Plants were incubated, at 18° C. with a 18/6 hr (light/dark) photoperiod for 12 days to allow disease symptoms to appear and subsequently assessed using a 0)-6 scale as described by Hammoudi et al., (2012): 0=no symptoms: 1=lesions on the infection site<1.5 mm: 2=lesions on the infection site 1.5-3.5 mm: 3=lesions on the infection site>3.0 mm: 4=grey to green tissue collapse 3.1-5.0 mm: 5=grey to green tissue collapse>5.0 mm (≤10 pycnidia): 6=grey to green tissue collapse>5.0 mm (>10 pycnidia). Newly emerging leaves were carefully removed during the experimental period. The mean score from 9 infected seedlings from each tray was used in the analysis. The experiment was repeated once.

Statistical analyses were performed using the software package R (R Core Team, 2019). A cumulative link mixed model (CLMM) from the "ordinal" R package was used to model the lesion severity scores using a flexible threshold for each cultivar. The fixed effects used in the model were the treatment group and analysis of Deviance was used to assess the significance of the fixed effects. There were 12 treatments (seed coated with several fungal strains, including several genetically diverse strains of *Beauveria bassiana, Beauveria pseudobassiana* and seed without any coating acting as a pathogen-only control), with 9 seedlings per treatment arranged in a randomised design.

*Beauveria bassiana* O2380 significantly (P<0.001) suppressed the amount of disease caused by *Leptosphaeria maculans* on leaves of forage kale (*Brassica oleracea*), cv. Firefly, after wounding, across two replicated experiments, compared to the pathogen-only control (Table 2). Other genetically diverse strains of *Beauveria bassiana* and *Beauveria pseudobassiana* did not significantly (P<0.001) suppress the amount of disease caused by *Leptosphaeria maculans* on leaves of forage kale, cv. Firefly (Table 2).

Disclosed herein is the inventors surprising determination that *Beauveria bassiana* strain O2380 is an effective biocontrol agent against *Leptosphaeria maculans*, the fungal pathogen responsible for the disease phoma stem canker (or blackleg disease) in *Brassica* spp.

a New Zealand isolate of *Mycoplasma* ovipneumoniae. Microbiology Resource Announcements 9.

Cardone, M., Mazzoncini, M., Menini, S., Rocco, V., Senatore, A., Seggiani, M., Vitolo, S., 2003. *Brassica carinata* as an alternative oil crop for the production of biodiesel in Italy: agronomic evaluation, fuel production by transesterification and characterization. Biomass Bioenergy 25, 623-636.

Cummings, N.J., 2009. Entomopathogenic fungi in New Zealand native forests: the genera *Beauveria* and *Isaria*. PhD thesis. Canterbury University, New Zealand.

Delourme, R., Falentin, C., Huteau, V., Clouet, V., Horvais, R., Gandon, B., Specel, S., Hanneton, L., Dheu, J. E., Deschamps, M., Margale, E., Vincourt, P., Renard, M.,

TABLE 2

Mean disease score (±SE) of forage kale, cv. Firefly, leaves after
wounding and inoculation by *Leptosphaeria maculans* following
treatment of seeds by several genetically diverse strains of *Beauveria*.
The results from two replicated experiments are shown.

| Treatment | Experiment 1 | | Experiment 2 | |
|---|---|---|---|---|
| | Mean disease score | SE | Mean disease score | SE |
| Pathogen-only control | 4.17 | 0.45 | 5.26 | 0.29 |
| Treatment 2 | 3.47 | 0.41 | 5.42 | 0.28 |
| *Beauveria bassiana* T3 | 3.64 | 0.47 | 5.12 | 0.33 |
| *Beauveria bassiana* T4 | 2.87 | 0.39 | 4.10 | 0.41 |
| Fungus T5 | 3.82 | 0.42 | 3.32 | 0.30 * |
| *Beauveria bassiana* T6 | 4.79 | 0.52 | 4.63 | 0.48 |
| *Beauveria bassiana* T7 | 4.36 | 0.39 | 4.89 | 0.34 |
| *Beauveria pseudobassiana* T8 | 3.93 | 0.45 | 4.42 | 0.36 |
| *Beauveria pseudobassiana* T9 | 3.20 | 0.45 | 4.94 | 0.33 |
| *Beauveria pseudobassiana* T10 | 3.75 | 0.39 | 3.56 | 0.36 |
| *Beauveria bassiana* O2380 | 1.85 | 0.35 * | 1.91 | 0.25 * |
| Fungus T12 | 2.45 | 0.51 | 5.17 | 0.36 |

* Mean disease score significantly (P < 0.001) lower compared to pathogen-only control.

Although the invention has been described by way of example and with reference to particular embodiments, it is to be understood that modifications and/or improvements may be made without departing from the scope of the invention.

In addition, where features or aspects of the invention are described in terms of Markush groups, those skilled in the art will recognise that the invention is also thereby described in terms of any individual member or subgroup of members of the Markush group.

INDUSTRIAL APPLICATION

Isolated *Beauveria bassiana* strain O2380, Brassicaceae host plant/*B. bassiana* strain O2380 combinations, seeds infected with *B. bassiana* strain O2380, methods of making *B. bassiana* strain O2380 and methods of using *B. bassiana* strain O2380 for biocontrol of phytopathogenic fungi as disclosed herein all have industrial application for the production of plants that are used for human and/or animal consumption.

REFERENCES

Ali, H., Ali, Z., Ali, H., Mehmood, S., Ali, W., 2007. In vitro regeneration of *Brassica napus* L., cultivars (Star, Cyclone and Westar) from hypocotyls and cotyledonary leaves. Pakistan Journal of Botany 39, 1251.

Bridgeman, B., Gupta, S., Murray, A., Dukkipati, V., Altermann, E., Wedlock, D., 2020. Draft genome sequence of 2006. Genetic control of oil content in oilseed rape (*Brassica napus* L.). Theoretical and Applied Genetics 113, 1331-1345.

Dixelius, C., Bohman, S., Wretblad, S., 2004. Disease Resistance. In: Douglas, C., Pua, E. (Eds.), Biotechnology in Agriculture and Forestry. Springer-Verlag, Berlin, pp. 253-271.

Dixon, G. R., 2007. Vegetable Brassicas and Related Crucifers. CABI Publishing, Wallingford, UK.

Fisher, J. J., Rehner, S. A., Bruck, D. J., 2011. Diversity of rhizosphere associated entomopathogenic fungi of perennial herbs, shrubs and coniferous trees. Journal of Invertebrate Pathology 106, 289-295.

Glare, T. R., Reay, S. D., Nelson, T. L., Moore, R., 2008. *Beauveria caledonica* is a naturally occurring pathogen of forest beetles. Mycological research 112, 352-360.

Gómez-Campo, C., 1980. Morphology and morpho-taxonomy of the tribe Brassiceae. In: Tsunoda, S., Hinata, K., Gómez-Campo, C. (Eds.), *Brassica* Crops and Wild Allies. Scientific Societies Press, Tokyo.

Graner, G., Persson, P., Meijer, J., Alström, S., 2003. A study on microbial diversity in different cultivars of *Brassica napus* in relation to its wilt pathogen, *Verticillium longisporum*. FEMS Microbiol. Lett. 224, 269-276.

Hammoudi, O., Salman, M., Abuamsha, R., Ehlers, R.-U., 2012. Effectiveness of bacterial and fungal isolates to control *Phoma lingam* on oilseed rape *Brassica napus*. American Journal of Plant Sciences 3, 773.

Jukes, T. H., Cantor, C. R., 1969. Evolution of protein molecules. Mammalian protein metabolism 3, 21-132.

Kearse, M., Moir, R., Wilson, A., Stones-Havas, S., Cheung, M., Sturrock, S., Buxton, S., Cooper, A., Markowitz, S., Duran, C., 2012. Geneious Basic: an integrated and extendable desktop software platform for the organization and analysis of sequence data. Bioinformatics 28, 1647-1649.

Körbitz, W., 1999. Biodiesel production in Europe and North America, an encouraging prospect. Renewable Energy 16, 1078-1083.

Korosi, G. A., Wilson, B. A., Powell, K. S., Ash, G. J., Reineke, A., Savocchia, S., 2019. Occurrence and diversity of entomopathogenic fungi (*Beauveria* spp. and *Metarhizium* spp.) in Australian vineyard soils. Journal of Invertebrate Pathology 164, 69-77.

Lob, S., 2014. *Leptosphaeria* diseases of oilseed rape and swede: identification and epidemiology. Faculty of Agriculture and Life Science. Lincoln University, Canterbury, New Zealand.

Medo, J., Michalko, J., Medová, J., Cagáň, L'., 2016. Phylogenetic structure and habitat associations of *Beauveria* species isolated from soils in Slovakia. Journal of Invertebrate Pathology 140, 46-50.

Mascarin, G. M., Jaronski, S. T. The production and uses of *Beauveria bassiana* as a microbial insecticide. World J Microbiol Biotechnol 32, 177 (2016).

Mckinnon, A. C., Saari, S., Moran-Diez, M. E. et al. *Beauveria bassiana* as an endophyte: a critical review on associated methodology and biocontrol potential. BioControl 62, 1-17 (2017).

Murashige, T., Skoog, F., 1962. A revised medium for rapid growth and bioassays with tobacco tissue cultures. Physiologia *Plantarum* 15, 473-497.

O'Donnell, K., Kistler, H. C., Cigelnik, E., Ploetz, R. C., 1998. Multiple evolutionary origins of the fungus causing Panama disease of banana: concordant evidence from nuclear and mitochondrial gene genealogies. Proceedings of the National Academy of Sciences 95, 2044-2049.

R Core Team, 2019. A Language and Environment for Statistical Computing. Vienna: R Foundation for Statistical Computing.

Rakow, G., 2004. Species origin and economic importance of *Brassica*. In: Nagata, T., Lörz, H., Widholm, J. M. (Eds.), Biotechnology in Agriculture and Forestry: Brassica. Springer, Berlin, Germany Rao, S., Horn, F., 1995. Cereals and Brassicas for forage. In: Barnes, R., Miller, D., Nelson, C. (Eds.), Forages: An Introduction to Grassland Agriculture. Iowa State University Press, Ames, USA, pp. 451-462.

Rehner, S. A., Buckley, E., 2005. A *Beauveria* phylogeny inferred from nuclear ITS and EF1-α sequences: evidence for cryptic diversification and links to *Cordyceps* teleomorphs. Mycologia 97, 84-98.

Rehner, S. A., Posada, F., Buckley, E. P., Infante, F., Castillo, A., Vega, F. E., 2006. Phylogenetic origins of African and neotropical *Beauveria bassiana* s.l. pathogens of the coffee berry borer, *Hypothenemus hampei*. Journal of Invertebrate Pathology 93, 11-21.

Salisbury, P., Ballinger, D., Wratten, N., Plummer, K., Howlett, B., 1995. Blackleg disease on oilseed *Brassica* in Australia: a review. Australian Journal of Experimental Agriculture 35, 665-672.

Saitou, N., Nei, M., 1987. The neighbor-joining method: a new method for reconstructing phylogenetic trees. Molecular Biology and Evolution 4, 406-425.

Sievers, F., Higgins, D. G., 2018. Clustal Omega for making accurate alignments of many protein sequences. Protein Science 27, 135-145.

Snowdon, R., Lühs, W., Friedt, W., 2006. Oilseed Rape. In: Kole, C., (Ed.), Genome Mapping and Molecular Breeding in Plants-Oilseeds. Springer, Berlin, Germany, pp. 54-114.

Warwick, S. I., Francis, A., Gugel, R. K., 2009. Guide to Wild Germplasm: *Brassica* and Allied Crops (Tribe Brassiceae, Brassicaceae). Agriculture and Agri-Food Canada.

West, J. S., Kharbanda, P. D., Barbetti, M. J., Fitt, B. D. L., 2001. Epidemiology and management of *Leptosphaeria maculans* (*phoma* stem canker) on oilseed rape in Australia, Canada and Europe. Plant Pathology 50, 10-27.

Zhang, X., Fernando, W. D., 2018. Insights into fighting against blackleg disease of *Brassica napus* in Canada. Crop and Pasture Science 69, 40-47.

Zimmermann. G. (2007). Review on safety of the entomopathogenic fungi *Beauveria bassiana* and *Beauveria brongniartii*. Biocontrol Science and Technology. 17 (6), 553-596.

Microorganism Deposits

Description of the Microorganism Deposits Made Under the Budapest Treaty

The following biological deposits have been made under the terms of the Budapest Treaty on the International Recognition of the Deposit of Micro-organisms for the Purposes of Patent Procedure.

| Deposit Identification Reference | International Depository Designation | Date of Deposit |
|---|---|---|
| DSM Accession #33860 | Leibniz Institute DSMZ-German Collection of Microorganisms and Cell Cultures | 26 Apr. 2021 |

We claim:

1. A method of conferring at least some level of fungal disease resistance on a host plant comprising artificially infecting the host plant with an isolated strain of *B. bassiana* *O2380*, representative sample having been deposited under accession DSM 33860 at Leibniz Institute DSMZ-German Collection of Microorganisms and Cell Cultures, to form a host plant/*B. bassiana* combination.

2. The method of claim 1, wherein artificially infecting comprises contacting the host plant with the isolated *B. bassiana* strain O2380 or a composition comprising the isolated strain of *Beauveria bassiana* strain O2380 and a carrier.

3. The method of claim 1, wherein the host plant is a Brassicaceae host plant selected from the group of *Brassica* spp. consisting of *Brassica balearica* (Mallorca cabbage); *Brassica carinata* (Abyssinian mustard or Abyssinian cabbage); *Brassica elongate* (elongated mustard); *Brassica fruticulose* (Mediterranean cabbage); *Brassica hilarionis* (St. Hilarion cabbage); *Brassica juncea* (Indian mustard, brown and leaf mustards, Sarepta mustard); *Brassica napus* (rapeseed, canola, rutabaga, Siberian kale); *Brassica narinosa* (broadbeaked mustard); *Brassica nigra* (black mustard); *Brassica oleracea* (kale, cabbage, collard greens, broccoli, cauliflower, kai-lan, Brussels sprouts, kohlrabi); *Brassica*
*perviridis* (tender green, mustard spinach); *Brassica rapa* syn. *B. campestris* (Chinese cabbage, turnip, rapini, komatsuna); *Brassica rupestris* (brown mustard); *Brassica spinescens* and *Brassica tournefortii* (Asian mustard).

4. The method of claim 1, wherein the *Brassica* spp. host plant is selected from the group of *B. napus, B. rapa, B. campestris* or *B. oleracea.*

5. The method of claim 1, wherein the *Brassica* spp. host plant is a subspecies or interspecific hybrid between any combination of *B. napus, B. rapa, B. campestris* and/or *B. oleracea.*

6. The method of claim 1, wherein the *Brassica* spp. host plant is selected form the group consisting of *B. campestris* ssp. *rapifera, B. napus* ssp. *biennisxB. oleracea* ssp. *acephala, B. oleracea* ssp. *acephala, B. napus* subsp. *napus,* and *B. napus* ssp. *biennis.*

7. The method of claim 1 wherein the isolated strain and/or the isolated strain is a composition in the form of spores and/or mycelium.

8. The method of claim 2 wherein the carrier is an agriculturally acceptable carrier selected from the group consisting of antioxidants, wetting agents, emulsifiers, fillers, growth stimulants, anti-caking agents, dispersants, surfactants and combinations thereof.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthesized

<400> SEQUENCE: 1
cargaygtbt acaagatygg tgg                                               23
```

-continued

```
<210> SEQ ID NO 2
<211> LENGTH: 24
<212> TYPE: DNA
<213> ORGANISM: Artificial Sequence
<220> FEATURE:
<223> OTHER INFORMATION: Synthesized

<400> SEQUENCE: 2
ccraacrgcr acrgtyygtc tcat                                                             24

<210> SEQ ID NO 3
<211> LENGTH: 18
<212> TYPE: DNA
<213> ORGANISM: Artificial Sequence
<220> FEATURE:
<223> OTHER INFORMATION: Synthesized

<400> SEQUENCE: 3
gtcgcagcca gagcaact                                                                    18

<210> SEQ ID NO 4
<211> LENGTH: 19
<212> TYPE: DNA
<213> ORGANISM: Artificial Sequence
<220> FEATURE:
<223> OTHER INFORMATION: Synthesized

<400> SEQUENCE: 4
agattcgcaa cgtcaactt                                                                   19
```